United States Patent [19]
Holroyd

[11] Patent Number: 5,473,315
[45] Date of Patent: Dec. 5, 1995

[54] ENHANCED MEANS OF PROCESSING SIGNALS USED TO INTERPRET THE CONDITION OF MACHINERY

[75] Inventor: Trevor J. Holroyd, Nr. Matlock, England

[73] Assignee: Holroyd Instruments Limited, Derbyshire, England

[21] Appl. No.: 298,947

[22] Filed: Aug. 31, 1994

[30] Foreign Application Priority Data

Sep. 23, 1993 [GB] United Kingdom ............... 9319640

[51] Int. Cl.$^6$ ................................................. G08B 21/00
[52] U.S. Cl. ......................................... 340/683; 381/56
[58] Field of Search ................................ 340/683; 381/56

[56] References Cited

U.S. PATENT DOCUMENTS

| | | | |
|---|---|---|---|
| 4,366,544 | 12/1982 | Shima et al. | 340/683 |
| 4,988,979 | 1/1991 | Sasaki et al. | 340/683 |

*Primary Examiner*—Glen Swann
*Attorney, Agent, or Firm*—Trexler, Bushnell, Giangiorgi & Blackstone, Ltd.

[57] ABSTRACT

A method of processing electrical signals which span a large dynamic range in order to enable the signal to be processed in its entirety without the need for any alteration to the signal gain or signal attenuation, comprises splitting of the signal along two or more paths each having a different amount of amplification or attenuation, the passing of each of these two or more different signals into one of two or more smaller dynamic range circuits which produce a logarithmically scaled representation of the average magnitude of the signal level at its input and the summation of the logarithmic outputs of the two or more smaller dynamic range circuits to produce a resultant logarithmically scaled signal representative of the average magnitude of the input signal over a very large dynamic range. The invention also includes apparatus for carrying out the above defined method.

19 Claims, 4 Drawing Sheets

ENHANCED MEANS OF PROCESSING SIGNALS USED TO INTERPRET THE CONDITION OF MACHINERY

FIELD OF THE INVENTION

The present invention relates to a method and an apparatus for processing electrical signals having a large dynamic range and is particularly of interest for processing signals from sensors or transducers sensitive to acoustic emissions or stress waves, noise signals and mechanical vibrations containing features indicative of the mechanical state or condition of machinery.

Acoustic Emission or stress wave activity is structure borne elastic waves associated with operating machinery and is produced as a result of friction, impacts, cavitation, metal removal, crack growth and plastic deformation taking place during the operation of the machinery.

Noise signals are airborne sound waves associated with operating machinery and are produced as a result of friction, impacts, cavitation, metal removal, crack growth and plastic deformation taking place during the operation of the machinery.

Mechanical vibrations within materials and structures are associated with operating machinery and are produced as a result of friction, impacts, cavitation, metal removal, crack growth and plastic deformation taking place during the operation of the machinery.

Acoustic emission, noise and vibration techniques have been used to monitor the condition of machinery, to assist in the detection and diagnosis of fault conditions sometimes at an early stage. The early detection of faults enables maintenance to be planned and replacement of degrading machinery with a minimum of disruption and cost.

DESCRIPTION OF THE PRIOR ART

In prior art methods of processing acoustic emission, noise and vibration a transducer, microphone or accelerometer detects the structure borne wave, airborne wave or mechanical distortion and produces an electrical signal which corresponds to the acoustic emission, noise or vibration activity. In a first method the level of the electrical signal is measured, for example the mean level or the root mean square (RMS) level.

A good component operating under normal conditions gives a relatively low electrical signal level whereas a bad component under normal conditions gives a relatively high electrical signal. A good component operating under adverse conditions also gives a relatively high electrical signal.

In a second method of processing the electrical signal the peak signal level of the electrical signal is measured. The peak signal level will be at least equal to the mean level and usually higher than the mean signal level. A good component operating under normal conditions has a peak level which is equal to or more usually a little higher than the mean level or root mean square level whereas a bad component under normal conditions gives a high peak signal level in relation to the mean level or root mean square level. A good component operating under adverse conditions can also give a high peak signal level in relation to the mean or root mean square level.

In a third method of processing the electrical signals the peak level is divided by the rms level and this ratio is referred to as the Crest Factor. A good component operating under normal conditions has a relatively low Crest Factor whereas a bad component under normal conditions has a relatively high Crest Factor. A good component operating under adverse conditions also gives a relatively high Crest Factor.

With each of the above signal processing methods the information in the signal is reduced to a single number or value which characterises the signal over a certain period of time (i.e. an averaging time). When information in signals is reduced to such an extent it is important that the processing circuitry is faithfully characterising the original electrical signal otherwise the processing will introduce errors whose presence may not be noticeable and cannot be corrected for later. Such errors may lead to the misinterpretation of the signals and a faulty diagnosis of the mechanical state of the component which generated the signals.

Considering all types of machinery operating under all conditions and in all states of mechanical condition the values of the electrical signal from a transducer, microphone or accelerometer applied to operating machinery in general can have values which extend over a large range. Therefore an instrument for general use designed to process these electrical signals must be able to accept electrical signals levels having values which extend over a large range. It is common for a general purpose instrument to be able to process signals which extend over a range of 10,000 to 1. However low cost circuitry cannot readily process signals over such a large range of signal levels with 100 to 1 being more typical especially for higher frequency signals. A number of methods are commonly used to achieve processing of signals over such a large range of levels using low cost circuitry.

In a first method the instrument is designed to process signals at any one time over a small range of values (e.g. 100 to 1). By means of one or more switches the electrical signals from the transducer, microphone or accelerometer can be amplified or attenuated by different amounts so as to alter the values of the electrical signal levels that can be processed. The switches can be activated either manually or automatically. However for this method to work it is essential that the signal is amplified or attenuated by the right amount for it to be within the working range of the processing core. For an accurate measurement it is essential that the signal levels giving rise to the highest peaks as well as the lowest troughs fall within the working range of the processing core. If this is not achieved (e.g. because of operator error) or cannot be achieved because the range of signals during the period of the measurement spans a range of levels greater than range of the processing core then the measurement will be in error. The amount of this error will not be known and cannot be accounted for later since it will be dependent upon the actual gain setting and the actual values of the signal levels during the period of the measurement. As signal levels increase with increasing distress or degradation within the operating machinery it will be necessary to reduce the gain or attenuate the signal in order to keep the signal levels within the working range of the signal processing core. Each time the gain is reduced or signal attenuated the error in the measurement will change in a step-wise manner.

In a second method the signal processing core of the instrument is designed to process signals over a small range of values (e.g. 100 to 1) and the electrical signal from the transducer, microphone or accelerometer is acted upon by an automatic gain control (AGC) circuit which has the effect of keeping the signal level within the appropriate range for the signal processing core. Typically the AGC detects the mean of the signal level and adjusts the gain to keep this within the working range of the processing core. However for an accurate measurement it is essential that the signal levels giving rise to the highest peaks as well as the lowest troughs fall within the working range of the processing core. If this cannot be achieved because the AGC cannot position the range of signals during the period of the measurement such that either the lowest troughs or the highest peaks fall within the working range of the processing core then the measurement will be in error. The amount of this error will not be known and cannot be accounted for but will be dependent upon the actual gain setting and the actual values of the signal levels during the period of the measurement. As signal levels increase with increasing distress or degradation within the operating machinery the AGC will reduce the gain or attenuate the signal in order to keep the sit-real levels within the working range of the signal processing core. As the gain is dynamically reduced or signal dynamically attenuated the error in the measurement will also change dynamically. The amount of this error will not be known and cannot be accounted for later.

In a third method the instrument is designed to process signals at any one time over a small range of values (e.g. 100 to 1) and the electrical signals from the transducer, microphone or accelerometer are amplified or attenuated by a normalising factor i.e. an amount depending upon the value of another variable associated with the machine or its operation such as its type, construction or speed. However for this method to work it is essential that the signal is amplified or attenuated by the right amount for it to be within the working range of the processing core. For an accurate measurement it is essential that the signal levels giving rise to the highest peaks as well as the lowest troughs fall within the working range of the processing core. If this is not achieved because of errors in the normalising factor or cannot be achieved because the range of signals during the period of the measurement spans a range of levels greater than range of the processing core then the measurement will be in error. The amount of this error will not be known and cannot be accounted for later but will be dependent upon the actual gain setting and the actual values of the signal levels during the period of the measurement.

Each of the three methods above attempts to enable a processing core of restricted dynamic range (e.g. 100 to 1) to process signals potentially having a much larger dynamic range (e.g. 10,000 to 1). In order for the measurement to be accurate each method assumes that the dynamic range of the signal during the measurement is less than the dynamic range of the processing core and can be accurately positioned within it. Failure for this to be achieved will not necessarily be immediately apparent in the measured value but will be a cause of error in the value and potentially therefore a misinterpretation in its meaning with respect to the condition of the machine on which the measurement is being taken.

SUMMARY OF THE INVENTION

The present invention seeks to provide a simple method and apparatus for processing electrical signals which overcomes the problems associated with the prior art methods and apparatus.

Accordingly the present invention provides a simple method of processing electrical signals which span large dynamic range in order to enable the signal to be processed in its entirety without the need for any alteration to the signal gain or signal attenuation to take into account different machine types, operating conditions or mechanical conditions, comprises the splitting of the signal along two or more paths each having a different amount of amplification or attenuation, the passing of each of these two or more different signals into one of two or more smaller dynamic range circuits which each produce an output which is a logarithmically scaled representation of the average magnitude of the signal at its input and the summation of the logarithmically scaled outputs of the two or more smaller dynamic range circuits to produce a resultant logarithmically scaled signal representative of the average magnitude of the input signal over a very large dynamic range.

Using this method two 100 to 1 dynamic range circuits can be linked to result in a circuit able to process signals having a dynamic range of 10,000 to 1 for example.

The electrical signals may correspond to tile Acoustic Emission, Noise or Vibration generated by an operating machine and detected by a transducer, microphone or accelerometer.

The smaller dynamic range circuits may be standard RMS to DC converter circuits having logarithmically scaled outputs with matching performance and output scaling.

The logarithmic outputs of the smaller dynamic range circuits may correspond to the logarithmic value of the mean square of their respective input signals.

The difference in gains between the different signal paths may correspond to the usable dynamic range of each of the smaller dynamic range circuits.

The logarithmic outputs of the two or more smaller dynamic range circuits may be clamped at preset values signals outside their intended dynamic range such that the summed value of the two or more logarithmic outputs does not suffer errors due to over-range or under-range signals at the input of any of the smaller dynamic range circuits.

BRIEF DESCRIPTION OF THE DRAWINGS

The present invention will be more fully described by way of example with reference to the accompanying drawings in which.

DETAILED DESCRIPTION OF THE PREFERRED EMBODIMENT

An apparatus 1 for processing Acoustic Emissions to recognise features indicative of variations in the mechanical condition of operating machinery. The apparatus 1 comprises a transducer 2 which is acoustically coupled to a machine which provides the source of Acoustic Emissions or Stress Waves. These Acoustic Emissions or Stress Waves are commonly generated as a result of impacts and frictional processes within the machine due to mechanical distress or mechanical degradation. The transducer 2 is arranged to detect the Acoustic Emissions or Stress Waves generated by or in the machine and produce an electrical signal dependent upon the Acoustic Emission or Stress Wave activity detected. The transducer 2 is commonly a piezo-ceramic element although more than one transducer may be used. Other suitable types of transducer include piezoelectric plastics, capacitative transducers, electromagnetic transducers and laser interferometers.

Figure 1:
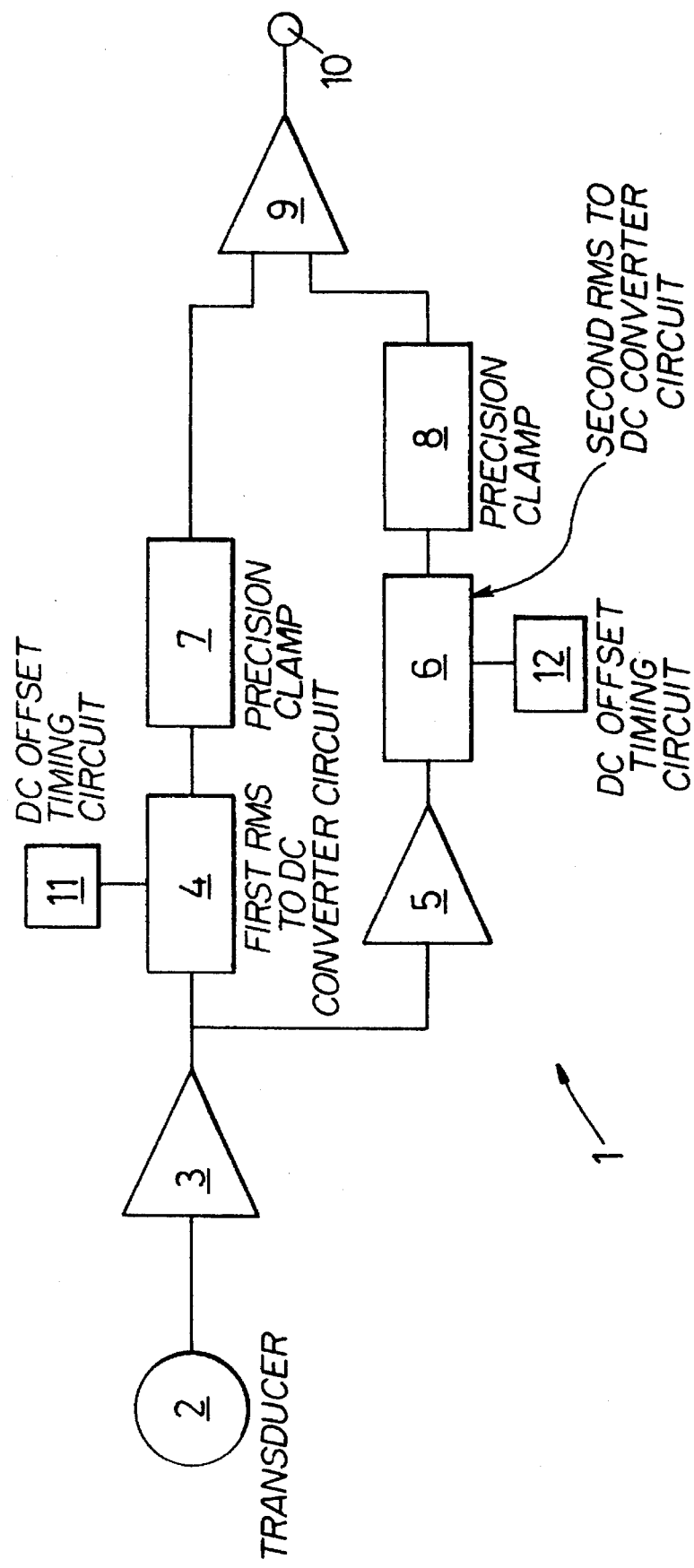
FIG. 1 is an apparatus for processing acoustic emission signals according to the present invention.
Figure 2:
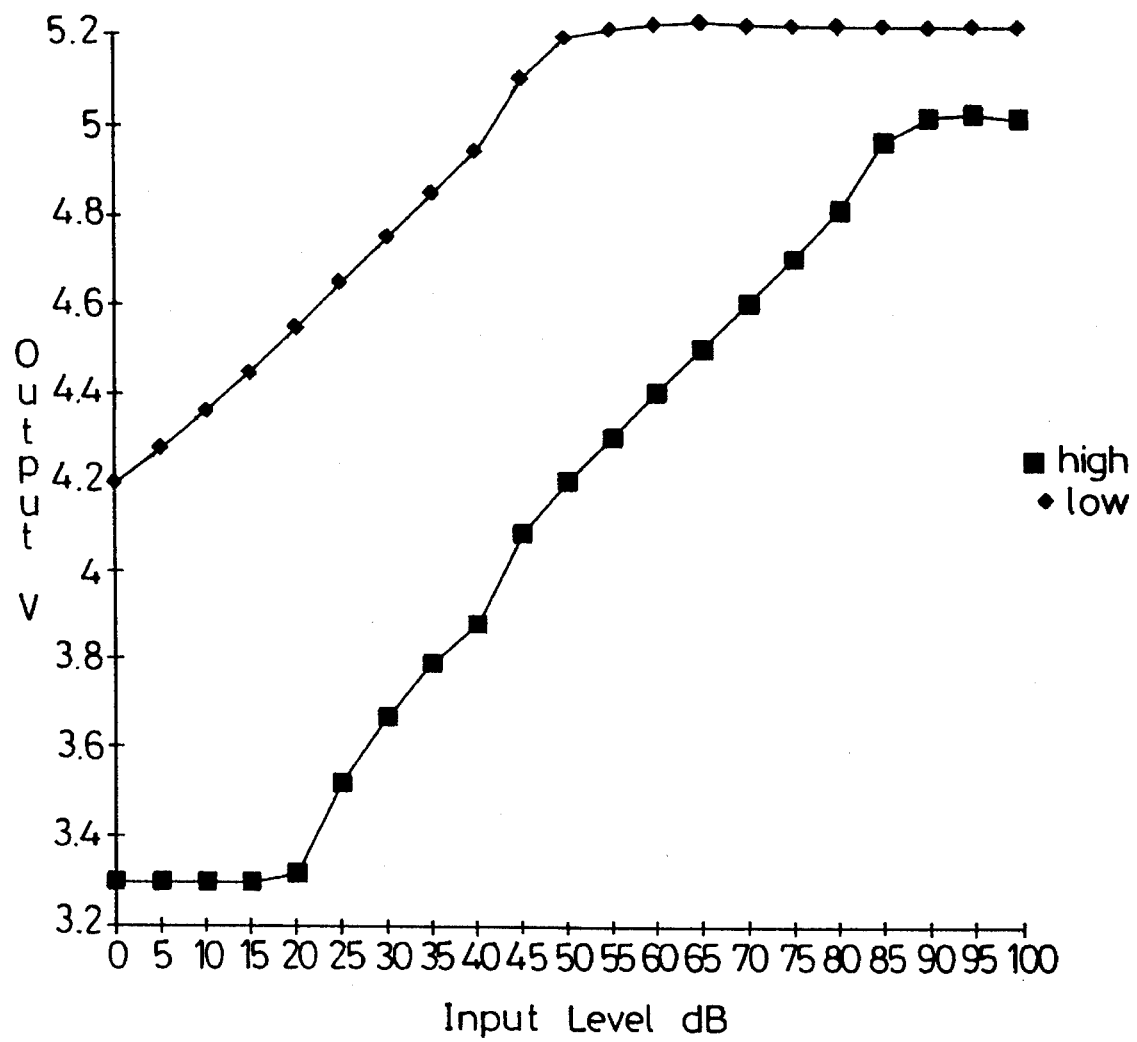
FIG. 2 is a graph showing the levels of the logarithmic outputs of two RMS to DC converters arranged according to the present invention for various signal levels from the transducer.

The electrical signal produced by the transducer 2 is supplied to the amplifier 3. The amplifier amplifies the electrical signal and may incorporate filters to select the required frequencies of operation. The amount of signal amplification within the amplifier 3 is chosen to suit the overall sensitivity of the circuit. The amplified electrical signal is then supplied in parallel (i.e. split into two paths) to a first RMS to DC converter circuit 4 having a usable dynamic range of approximately 40 dB and to a further amplifier 5 having a gain of 40 dB. The output of the amplifier 5 is supplied to a second RMS to DC converter 6 having a usable dynamic range of approximately 40 dB. The two RMS to DC converters 4 and 6 have matching performance and each provide an output which is a logarithmically scaled representation of the average magnitude of their input signal. In addition the two RMS to DC converters 4 and 6 when incorporated in the apparatus 1 are responsive to signals within a different range because of the higher amplification of the signals being supplied to the second RMS to DC converter 6. Hence RMS to DC converter 4 is best suited to operating on higher level signals and RMS to DC converter 6 is best suited to operating on lower level signals. The logarithmic output of the two RMS to DC converters 4 mid 6 are shown in FIG. 2 for a range of signal levels from the transducer. It is clear from the two traces in FIG. 2 that the most accurate logarithmic output for either of the RMS to DC converters 4 or 6 occurs when the output lies between 4 and 5 volts and this is referred to as the usable dynamic range.

Figure 3:
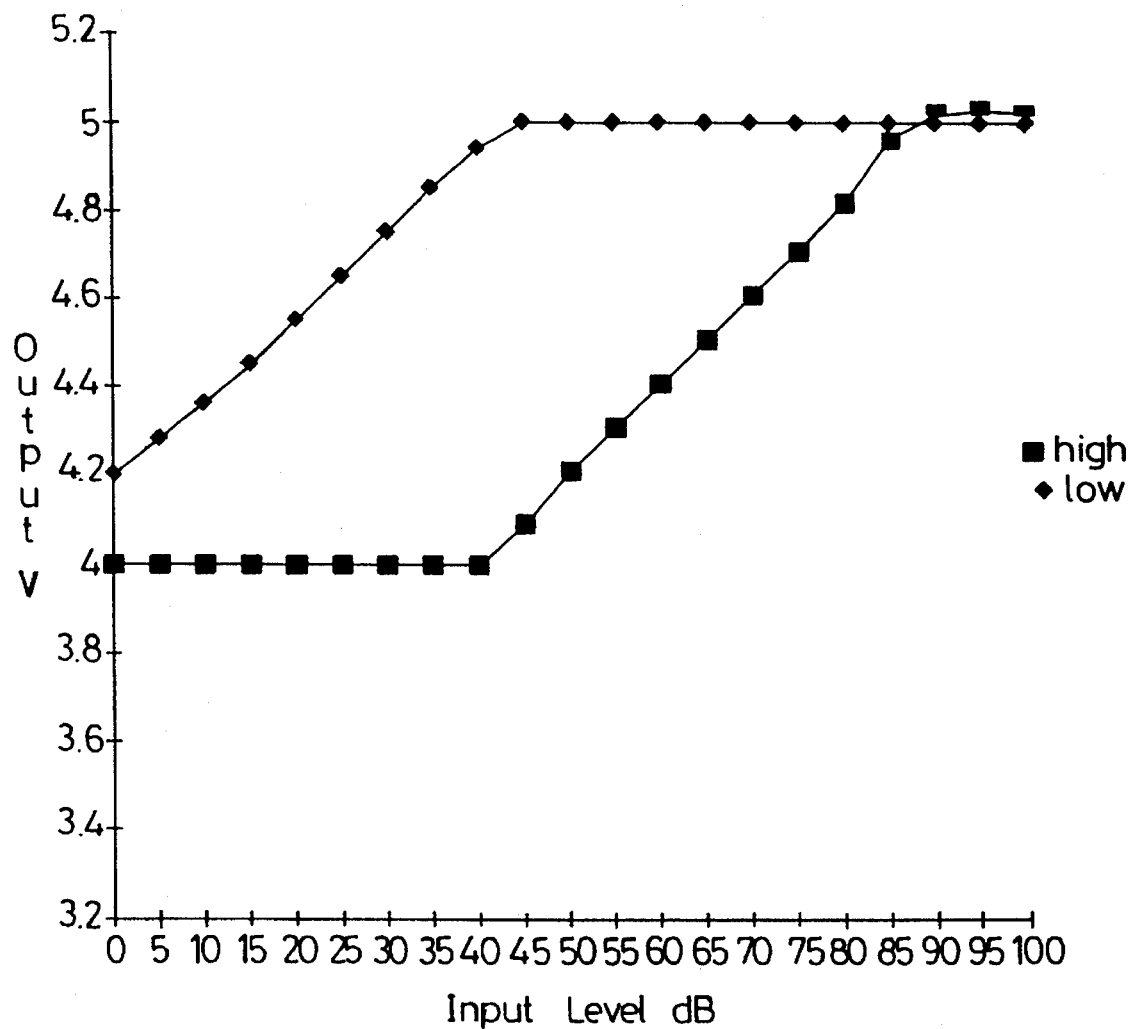
FIG. 3 is a graph showing the outputs of the two clamping circuits arranged according to the present invention for various signal levels from the transducer.
Figure 4:
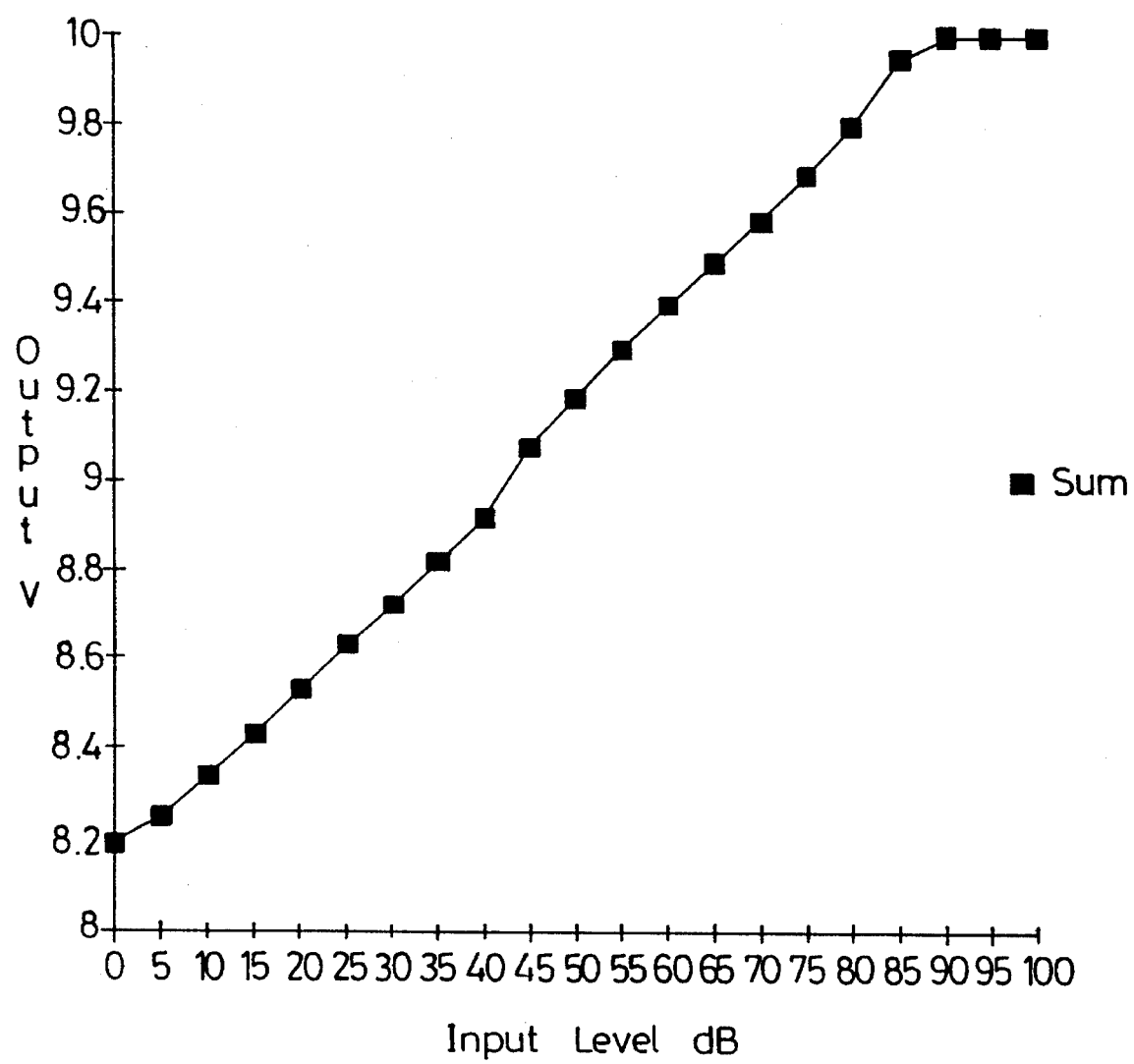
FIG. 4 is a graph of the summed value of the two logarithmic outputs arranged according to the present invention for signal levels from the transducer.

The logarithmic outputs of the RMS to DC converter 4 is supplied to a precision clamp 7 which ordinarily passes the signal level at its input to its output but clamps the output at 4 volts when the signal level at its input drops below its useful operating range. The logarithmic output of the RMS to DC converter 6 is supplied to a precision clamp 8 which ordinarily passes the signal level at its input to its output but clamps the output at 5 volts when the signal level at its input exceeds its useful range. The outputs of the precision clamps 7 and 8 in response to a range of transducer signal levels are shown in FIG. 3. The outputs of precision clamp 7 and precision clamp 8 are supplied to a precision summing amplifier 9 which has an output at a voltage level equal to the sum of the two voltage levels applied to its input. The output of the precision summing amplifier 9 is supplied to the output terminal 10. FIG. 4 is a graph of the signal level at the output terminal 10 for a range of signal levels from the transducer. In practice it is usually necessary to adjust the DC offset trimming circuits 11 and 12 in order to achieve a best match at the cross-over between the two RMS to DC converters 4 and 6 as the input level is varied.

The time constant for the RMS to DC conversion process within the RMS to DC converters 4 and 6 can be made short (e.g. 100 microseconds) so that the output signal from the precision summing amplifier 9 is a dynamic logarithmically scaled representation of the average magnitude of the input signal and retains much of the useful information contained within the original transducer signal. The output terminal 10 may be connected to a means of display, or may be connected to a means of analogue to digital conversion to enable digital analysis, or may be connected to additional signal processing circuitry to reveal the mean signal level and the peak signal level, or may be connected to additional signal processing circuitry to characterise the fine structure of the activity such as the number of signal peaks, the times of occurrence of peaks, the magnitudes of peaks and the shapes of peaks.

This method has the advantage of allowing transducer signals with a very large dynamic range (e.g. 80 dB or 10,000 to 1) to be processed without the need to change the gain of the circuit in any way.

This method also has the advantage of having a processing core consisting of elements which have only a small usable dynamic range (e.g. 40 dB or 100 to 1) and are readily available.

This method also has the advantage of providing a logarithmic dynamic signal which although representative of a transducer signal having a very large dynamic range has itself a much reduced dynamic range making it easier to further process.

I claim:

1. A method of processing electrical signals which span a large dynamic range in order to enable the signal to be processed in its entirety without the need for the signal gain or signal attenuation to be dynamically altered by an amount determined by the signal level, comprises splitting of the signal along two or more paths each having a different amount of amplification or attenuation, the passing of each of these two or more different signals into one of two or more smaller dynamic range circuits which produce a logarithmically scaled representation of the average magnitude of the signal level at its input and the summation of the logarithmic outputs of the two or more smaller dynamic range circuits to produce a resultant logarithmically scaled signal representative of the average magnitude of the input signal over said large dynamic range.

2. A method as claimed in claim 1 in which the logarithmic outputs of the two or more smaller dynamic range circuits are adjusted by means of trimming the level of their DC voltage offsets with respect to each other in order to correct for minor errors in the level of their outputs in order to produce a resultant output which has the closest approximation to logarithmic scaling over the entire dynamic range of input signals after summation.

3. A method as claimed in claim I in which the logarithmic outputs of the smaller dynamic range circuits correspond to the logarithmic value of the mean square of their respective input signals.

4. A method as claimed in claim 1 in which a difference in gains between the different signal paths is selected which is approximately equal to the usable dynamic range of each of the smaller dynamic range circuits.

5. A method as claimed in claim 1 in which the logarithmic outputs of the two or more smaller dynamic range circuits are clamped at preset values for signals outside their intended dynamic range such that the summed value of the two or more logarithmic outputs does not suffer errors due to over-range or under-range signals at the input of any of the smaller dynamic range circuits.

6. A method as claimed in claim 1 in which the electrical signals correspond to the acoustic emission or stress wave activity generated by an operating machine.

7. A method as claimed in claim 1 in which the electrical signals correspond to the vibrational activity generated by an operating machine.

8. A method as claimed in claim 1 in which the electrical signal correspond to the airborne noise generated by an operating machine.

9. An electronic apparatus for carrying out the method in claim 1 in which an electrical signal which spans a large dynamic range is processed in order to enable the signal in its entirety to be processed without the need for the signal gain or signal attenuation to be dynamically altered by an amount determined by the signal level, comprises means for splitting of the signal along two or more paths each having a different amount of amplification or attenuation, means to pass each of these two or more different signals into one of two or more smaller dynamic range circuits which produce a logarithmically scaled representation of the average magnitude of the signal level at its input and the summation of the logarithmic outputs of the two or more smaller dynamic range circuits to produce a resultant logarithmically scaled signal representative of the average magnitude of the input signal over said large dynamic range.

10. An apparatus as claimed in claim 9 in which the logarithmic outputs of the two or more smaller dynamic range circuits are adjusted by means of trimming the level of their DC voltage offsets with respect to each other in order to correct for minor errors in the level of their outputs in order to produce a resultant output which has the closest approximation to logarithmic scaling over the entire dynamic range of input signals after summation.

11. An apparatus as claimed in claim 9 in which the logarithmic outputs of the smaller dynamic range circuits correspond to the logarithmic value of the mean square of their respective input signals.

12. An apparatus as claimed in claim 9 in which a difference in gains between the different signal paths is selected which is approximately equal to the usable dynamic range of each of the smaller dynamic range circuits.

13. An apparatus as claimed in claim 9 in which the logarithmic outputs of the two or more smaller dynamic range circuits are clamped at preset values for signals outside their intended dynamic range such that the summed value of the two or more logarithmic outputs does not suffer errors due to over-range or under-range signals at the input of any of the smaller dynamic range circuits.

14. An apparatus as claimed in claim 9 comprising at least one transducer acoustically coupled to a process producing acoustic emissions and arranged to detect the acoustic emissions and to produce an electrical signal dependent upon the acoustic emission activity.

15. An apparatus as claimed in claim 9 comprising at least one accelerometer coupled to a process producing vibrations and arranged to detect the vibrations and to produce an electrical signal dependent upon the vibrational activity.

16. An apparatus as claimed in claim 9 comprising at least one microphone air coupled to a process producing noise and arranged to detect the airborne noise and to produce an electrical signal dependent upon the airborne noise activity.

17. An apparatus as claimed in claim 9 in which a means to determine the resultant logarithmically scaled signal representative of the average magnitude of the input signal over a very large dynamic range is used as part of equipment to determine the mechanical condition of operating machinery.

18. An electronic apparatus for processing electrical signals which span a large dynamic range in order to enable the signal to be processed in its entirety without the need for the signal gain or signal attenuation to be dynamically altered by the amount determined by the signal level, said electronic apparatus comprising;

means for splitting of the signal along at least two paths, each path having a different amount of amplification or attenuation;

a smaller dynamic range circuit coupled to each of said at least two paths for producing a logarithmically-scaled representation of the average magnitude of the signal level at its input; and means for summing logarithmically scaled representations coupled to the output of said at least two smaller dynamic range circuits for producing a resultant logarithmically-scaled signal representative of the average magnitude of the input signal over said large dynamic range.

19. An electronic apparatus for processing electrical signals spanning a large dynamic range which processes the signal in its entirety without the need for dynamically altering the signal gain or signal attenuation by an mount determined by the signal level, said electronic apparatus comprising;

input means for sensing physical phenomenon, such as acoustic emissions, vibration, and noise;

a first amplifier coupled to said input means;

a first root mean square to DC converter coupled to the said output of first amplifier;

a first precision clamp coupled to said first root mean square to DC converter;

a first DC offset timing circuit coupled to said first root mean square to DC converter;

a second amplifier coupled to the output of said first amplifier;

a second root mean square to DC converter coupled to said second amplifier;

a second DC offset timing circuit coupled to said second root mean squared DC converter;

a second precision clamp coupled to the output of said second root mean square to DC converter; and a summing amplifier coupled to the outputs said first precision clamp and said second precision clamp producing an output voltage level equal to the sum of the output voltage levels from the first dynamic range circuit and from the second dynamic range circuit.

* * * * *